United States Patent [19]
Authelin et al.

[11] Patent Number: 6,002,022
[45] Date of Patent: Dec. 14, 1999

[54] METHOD FOR PREPARING 4, 10-DIACETOXY-2α-BENZOYLOXY-5β, 20-EPOXY-1, 7β-DIHYDROXY-9-OXO-TAX-11-EN-13α-YL(2R,3S)-3-BENZOYLAMINO-2-HYDROXY-3-PHENYLPROPIONATE TRIHYDRATE

[75] Inventors: Jean-René Authelin, Saint-Germain-lès-Arpajon; Eric Didier, Paris; Franck Leveiller, Thiais; Isabelle Taillepied, Maisons-Alfort, all of France

[73] Assignee: Rhone-Poulenc Rorer S.A., Antony, France

[21] Appl. No.: 08/875,625

[22] PCT Filed: Jan. 23, 1996

[86] PCT No.: PCT/FR96/00104

§ 371 Date: Jul. 24, 1997

§ 102(e) Date: Jul. 24, 1997

[87] PCT Pub. No.: WO96/22984

PCT Pub. Date: Aug. 1, 1996

[30]   Foreign Application Priority Data

Jan. 25, 1995 [FR] France ................................ 95 00816

[51] Int. Cl.$^6$ .................................................. C07D 305/14
[52] U.S. Cl. ............................................. 549/510; 549/511
[58] Field of Search ...................................... 549/510, 511

[56]   References Cited

PUBLICATIONS

Wani et al, J. American Chemical Society, vol. 93 (9), May 1971, pp. 2325–2327.

*Primary Examiner*—Ba K. Trinh
*Attorney, Agent, or Firm*—Finnegan, Henderson, Farabow, Garrett & Dunner, L.L.P.

[57]   ABSTRACT

A process for the preparation of 4,10-diacetoxy-2α-benzoyloxy-5β,20-epoxy-1,7β-dihydroxy-9-oxo-tax-11-en-13α-yl (2R,3S)-3-benzoylamino-2-hydroxy-3-phenylpropionate trihydrate by crystallization from a water/alcohol solution.

8 Claims, 2 Drawing Sheets

METHOD FOR PREPARING 4,10-DIACETOXY-2α-BENZOYLOXY-5β, 20-EPOXY-1, 7β-DIHYDROXY-9-OXO-TAX-11-EN-13α-YL(2R,3S)-3-BENZOYLAMINO-2-HYDROXY-3-PHENYLPROPIONATE TRIHYDRATE

This application is a 371 application of PCT/FR96/00104 dated Jan. 23, 1996.

The present invention relates to a process for the preparation of 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate trihydrate.

4,10-Diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate (or paclitaxel) has noteworthy anticancer and antileukaemia properties.

4,10-Diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate may either be isolated from yew bark or prepared from baccatin III or from 10-desacetylbaccatin III according to the processes which are described more particularly in European patent applications EP 0,336,840 or EP 0,400,971 or in PCT international application WO 94/07878.

It has been found that 4,10-diacetoxy-2α-benzoyloxy-5β,20-epoxy-1,7β-dihydroxy-9-oxotax-11-en-13α-yl (2R,3S)-3-benzoylamino-2-hydroxy-3 -phenylpropionate trihydrate has a stability which is markedly superior to that of the anhydrous product.

According to the invention, 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate trihydrate may be obtained after crystallization of 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate from a mixture of water and an aliphatic alcohol containing 1 to 3 carbon atoms, followed by drying of the product obtained under reduced pressure and then maintaining in a relative humidity of greater than 20% at a temperature in the region of 25° C.

Figures 1A, 1B:
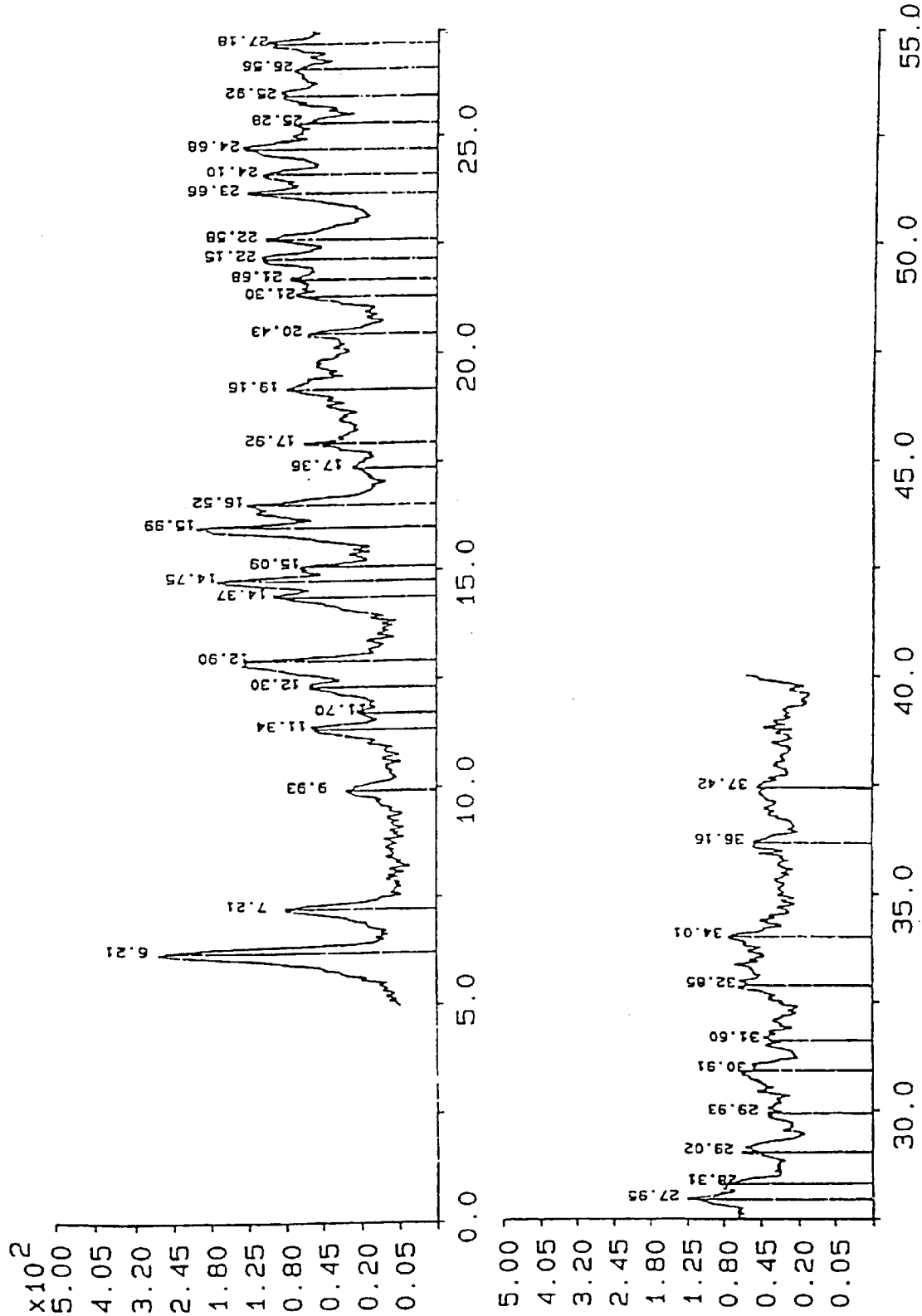
FIG. 1a is an X-ray powder diagram of a product of the present invention.
FIG. 1b is an X-ray powder diagram of a product of the present invention.

In order to carry out the process according to the invention, it may be particularly advantageous

- to dissolve or suspend the 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate in an aliphatic alcohol containing 1 to 3 carbon atoms,
- to treat the solution or the suspension with water optionally containing an inorganic base such as sodium hydrogen carbonate,
- to separate the crystals obtained, then
- to dry them under reduced pressure, and then optionally to maintain them in an atmosphere whose relative humidity is greater than 20% at a temperature in the region of 25° C.

Generally, the 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate is dissolved in an excess of the aliphatic alcohol, preferably methanol. The amount of alcohol is preferably between 6 and 12 parts by weight relative to the 4,10-diacetoxy-2α-benzoyloxy-5β, 20-epoxy-1,7β-dihydroxy-9-oxotax-11-en-13α-yl (2R,3S)-3-benzoylamino-2-hydroxy-3-phenylpropionate used.

Generally, water is added such that the water/alcohol weight ratio is between 3/1 and 1/3. The water added may contain up to 10% (w/v) of an inorganic base such as sodium hydrogen carbonate, so that the pH of the reaction mixture is above or equal to 7, preferably between 7 and 8, before separation of the crystals.

The 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate trihydrate which crystallizes is separated out, preferably by filtration or centrifugation, and then dried. The drying is carried out under reduced pressure, between 1 and 7 kPa, at a temperature in the region of 40° C. and the product obtained is optionally maintained in an atmosphere whose relative humidity is greater than 20% and at a temperature of between 0 and 60° C., preferably in the region of 25° C.

In order to carry out the process, it may be advantageous to perform the crystallization in the presence of ascorbic acid which is added during the dissolution or suspending of the 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate in the alcohol. It is possible to use up to 1% by weight of ascorbic acid.

4,10-Diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate trihydrate has been studied by thermogravimetric and differential calorimetric analyses and by X-ray diffraction.

More particularly, the thermogravimetric analysis shows a loss of mass between 25 and 140° C. in the region of 6%, which corresponds to three molecules of water per one molecule of 4,10-diacetoxy-2α-benzoyloxy-5β,20-epoxy-1, 7β-dihydroxy-9-oxotax-11-en-13α-yl (2R,3S)-3-benzoylamino-2-hydroxy-3-phenylpropionate.

In order to carry out the process according to the invention, when semi-synthetic paclitaxel is used, which is obtained according to the processes described, for example, in European patents EP 0,336,840 or EP 0,400,971 or in international PCT application WO 94/07878 which lead to a paclitaxel intermediate whose hydroxyl functions are protected, it is possible to work directly on the 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate solution or suspension obtained after removal of the protecting groups from the hydroxyl functions of the taxane ring and of the side chain. For example, by working under the conditions of international PCT application WO 94/07878, the intermediate 4,10-diacetoxy-2α-benzoyloxy-5β,20-epoxy-1-hydroxy-7β-triethylsilyloxy-9-oxotax-11-en-13α-yl (4S,5R)-3-benzoyl-2-(4-methoxyphenyl)-4-phenyl-1,3-oxazolidine-5-carboxylate is obtained in which the protecting groups may be removed using trifluoroacetic acid in methanol.

The examples which follow illustrate the present invention.

EXAMPLE 1

5.014 g of 4,10-diacetoxy-2α-benzoyloxy-5β,20-epoxy-1-hydroxy-7β-triethylsilyloxy-9-oxotax-11-en-13α-yl (4S, 5R)-3-benzoyl-2-(4-methoxyphenyl)-4-phenyl-1,3-oxazolidine-5-carboxylate assaying at 98% (4.52 mmol) and 50 cm³ of methanol were introduced into a reactor sheltered from the light. 7 cm³ of trifluoroacetic acid were added rapidly to the stirred white suspension. The temperature rose to about 35° C. After cooling to a temperature of about 5° C., 110 cm³ of aqueous 6% (w/v) sodium hydrogen carbonate solution were added. The pH is equal to 7. The crystals are separated out by filtration on a sinter funnel and are washed 4 times with 15 cm³ of a methanol/water mixture (30/70 by volume). After drying under reduced pressure at 35° C., 3.676 g of 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate assaying at 93.1% and containing about 4.8% water are obtained.

The product obtained is characterized by the X-ray powder diagram represented in FIG. 1.

The yield of pure product is 89.3% relative to the ester used.

Figures 2A, 2B:
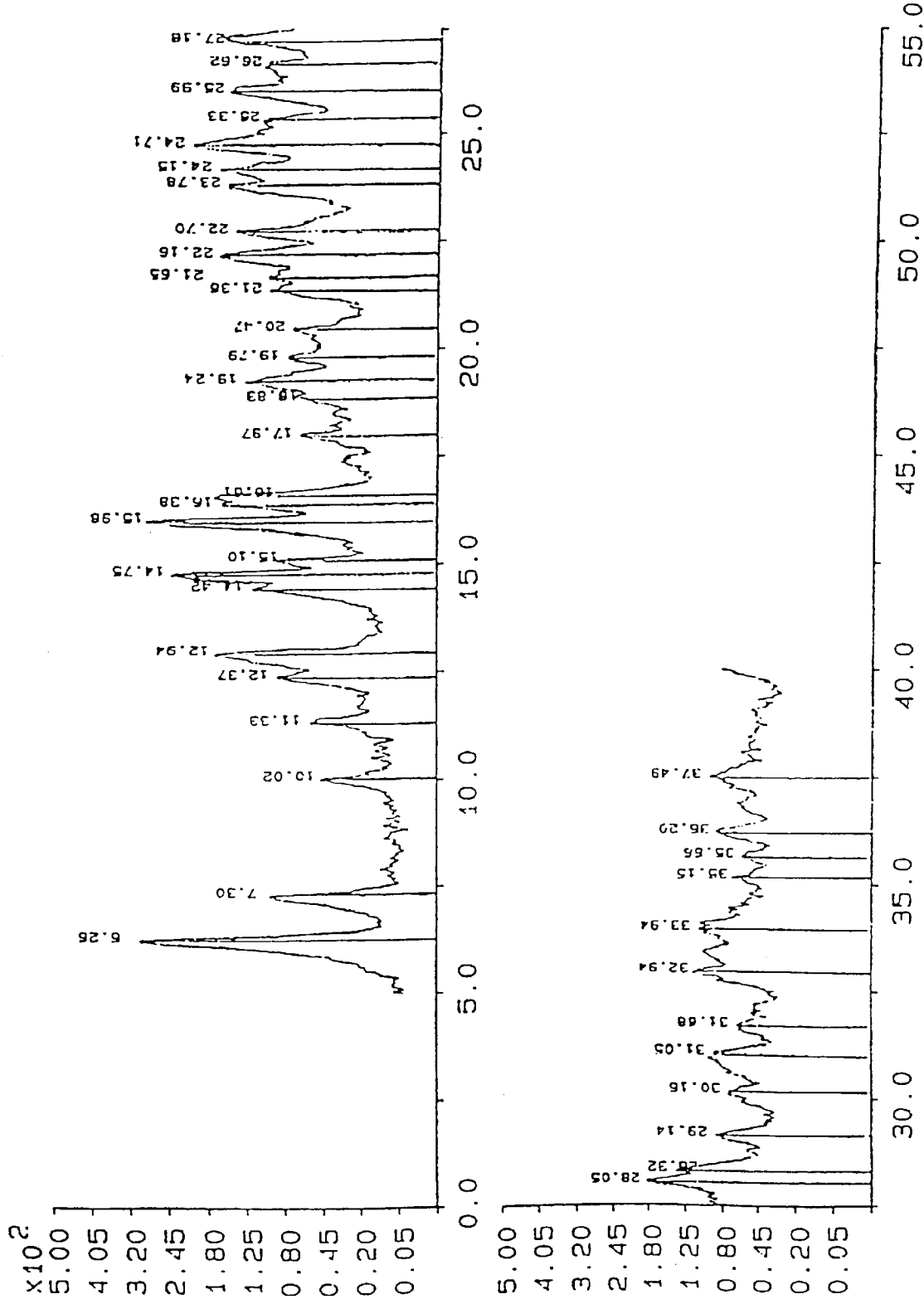
FIG. 2a is an X-ray powder diagram of a product of the present invention.
FIG. 2b is an X-ray powder diagram of a product of the present invention.

When maintained under relative humidity conditions of greater than 20%, the product stabilizes with a water content of about 6%. The XRPD diagram (X-ray powder diagram), represented in FIG. 2, shows that the product thus obtained is in the form of a trihydrate (theoretical value of the water content in the 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate trihydrate of 5.95%).

The X-ray powder diagram is obtained using a Philips PW 1700® machine with a cobalt anti-cathode tube ($\lambda$ $K_{\alpha I}$= 1.7889 Å), the sweeping being performed at an initial sweep angle of 5° 2-θ, final sweep angle of 40° 2-θ, with an increment of 0.02° 2-θ at a rate of 1 second per increment and using a silicon pastille.

EXAMPLE 2

3.006 g of 4,10-diacetoxy-2α-benzoyloxy-5β,20-epoxy-1-hydroxy-7β-triethylsilyloxy-9-oxotax-11-en-13α-yl (4S,5R)-3-benzoyl-2-(4-methoxyphenyl)-4-phenyl-1,3-oxazolidine-5-carboxylate assaying at 98% (2.70 mmol) and 30 cm³ of methanol are introduced into a reactor sheltered from the light. 6.3 cm³ of 99% trifluoroacetic acid are added to the stirred white suspension. After cooling to a temperature of about 5° C., 7.5 cm³ of demineralized water are added over 15 minutes. The crystals are separated out by filtration on a sinter funnel and are washed 3 times with 5 cm³ of a methanol/water mixture (80/20 by volume) at 5° C. After drying under reduced pressure at 35° C., 1.989 g of 4,10-diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate are obtained, assaying at 97.8% and containing about 6.8% water.

The yield is 84.3% relative to the ester used.

We claim:

1. A process for the preparation of 4,10-diacetoxy-2α-benzoyloxy-5β,20-epoxy-1,7β-dihydroxy-9-oxo-tax-11-en-13α-yl (2R,3S)-3-benzoylamino-2-hydroxy-3-phenylpropionate trihydrate, comprising crystallizing 4,10-diacetoxy-2α-benzoyloxy-5β,20-epoxy-1,7β-dihydroxy-9-oxo-tax-11-en-13α-yl (2R,3S)-3-benzoylamino-2-hydroxy-3-phenylpropionate from a mixture with water and an aliphatic alcohol containing 1 to 3 carbon atoms, wherein the water/alcohol weight ratio is between 3/1 and 1/3, and drying the product obtained under reduced pressure.

2. The process according to claim 1, wherein the alcohol is methanol.

3. The process according to claim 1, wherein the drying is carried out at a temperature in the region of 40 reduced pressure.

4. The process according to claim 1, wherein the crystallization is carried out in the presence of ascorbic acid.

5. The process according to claim 1, wherein the process is performed in situ on the ester resulting from the esterification of baccatin III in which the 13-hydroxy function is protected, with a protected β-phenylisoserine derivative after removal of the protecting groups.

6. 4,10-Diacetoxy-2α-benzoyloxy-5β,20-epoxy-1,7β-dihydroxy-9-oxotax-11-en-13α-yl (2R,3S)-3-benzoylamino-2-hydroxy-3-phenylpropionate trihydrate.

7. The process according to claim 1, wherein the product obtained stabilizes at about 6% water in an atmosphere in which the relative humidity is greater than 20%.

8. A process for the preparation of 4,10-diacetoxy-2α-benzoyloxy-5β,20-epoxy-1,7β-dihydroxy-9-oxo-tax-11-en-13α-yl (2R,3S)-3-benzoylamino-2-hydroxy-3-phenylpropionate trihydrate, comprising crystallizing 4,10-diacetoxy-2α-benzoyloxy-5β,20-epoxy-1,7β-dihydroxy-9-oxo-tax-11-en-13α-yl (2R,3S)-3-benzoylamino-2-hydroxy-3-phenylpropionate from a mixture with water and an aliphatic alcohol containing 1 to 3 carbon atoms, wherein the water/alcohol weight ratio is between 3/1 and 1/3, and drying the product obtained under reduced pressure, wherein the product is maintained under relative humidity conditions of greater than 20%.

* * * * *